(12) United States Patent
Moghissi et al.

(10) Patent No.: US 6,772,622 B2
(45) Date of Patent: Aug. 10, 2004

(54) DISBONDED COATING CATHODIC PROTECTION MONITORING COUPON

(75) Inventors: Oliver C. Moghissi, San Antonio, TX (US); Darrell S. Dunn, San Antonio, TX (US); Narasi Sridhar, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 197 days.

(21) Appl. No.: 10/092,482

(22) Filed: Mar. 8, 2002

(65) Prior Publication Data

US 2002/0194905 A1 Dec. 26, 2002

Related U.S. Application Data (60) Provisional application No. 60/274,231, filed on Mar. 9, 2001.

(51) Int. Cl.[7] ................................................. G01N 17/00
(52) U.S. Cl. ........................................................... 73/86
(58) Field of Search ............................... 73/86; 324/404

(56) References Cited

U.S. PATENT DOCUMENTS

| | | | | |
|---|---|---|---|---|
| 4,945,758 A | * | 8/1990 | Carpenter | .................... 73/86 |
| 5,391,686 A | | 2/1995 | Jadhav et al. | |
| 5,469,048 A | * | 11/1995 | Donohue | .................. 324/71.1 |
| 5,639,959 A | * | 6/1997 | Reiber | ........................ 73/86 |
| 5,728,943 A | | 3/1998 | Colter, Jr. et al. | |
| 5,814,982 A | | 9/1998 | Thompson et al. | |
| 6,060,877 A | | 5/2000 | Nekoksa | |
| 6,107,811 A | | 8/2000 | Caudill et al. | |

FOREIGN PATENT DOCUMENTS

WO WO 98/50788 11/1998

* cited by examiner

*Primary Examiner*—Robert Raevis
(74) *Attorney, Agent, or Firm*—Oliff & Berridge, PLC (57) ABSTRACT

A coupon for monitoring cathodic protection includes a metallic coupon structure on the outer surface of which at least one type of coating disbondment geometry anticipated on a pipeline is fabricated.

20 Claims, 7 Drawing Sheets

Fig. 1(a)

Rectangular disbondment with a holiday defect at one end

Fig. 1(b)

A circular disbondment with a small gap and a crack in the middle

Fig. 1(c)

Disbondment along overlap of a spirally wound tape coating and a holiday at one section

Test 1 polarization and pH data collected under a coating disbondment and adjacent exposed defect.

Fig. 7 Test 2 polaraization data collected at an exposed defect and under an adjacent coating disbondment.

DISBONDED COATING CATHODIC PROTECTION MONITORING COUPON

BACKGROUND OF THE INVENTION

1. Field of Invention

The present invention relates to a coupon, generally used for monitoring conditions that could lead to corrosion or stress corrosion cracking under a disbanded coating on a metallic surface. More particularly, the present invention relates to a steel coupon, preferably in the form of a pipe segment, on the outer diameter of which various types of coating disbondment geometries anticipated on a pipeline are fabricated, and in which the environment of the coating disbondment geometries can be continuously or periodically monitored and/or measured.

2. Description of Related Art

Metallic surfaces, such as are common in the field of pipelines and related structures, such as buried tanks and distribution systems, are adversely affected by numerous corrosive electrolytic fluids that contact these surfaces. For example, in the natural gas and petroleum industries, corrosion occurs extensively on the outer surface of both buried and above-ground pipelines.

In order to reduce, or preferably entirely eliminate, this undesirable metallic surface corrosion, anti-corrosion protective coatings have been extensively used in the pipeline industry. These ubiquitous anti-corrosion protective coatings frequently take the form of a helically-applied tape-like protective outerwrapping. The tape-like protective component may be applied directly over an unprepared pipeline outer surface, or may, in fact, be overlaid onto a primer-coated, pretreated pipeline outer surface. Other forms of protective coatings also exist, including coal tar epoxy, asphalt, and fusion bonded epoxy coatings.

For example, U.S. Pat. No. 5,391,686 discloses an exemplary pipeline coating material. The patent discloses a polyurethane formulation that is described to be especially effective as a corrosion preventing coating for metallic substrates. The polyurethane is prepared by mixing two components, one being a mixture of high and low molecular weight polyol compounds and the other being a polymeric methylene polyphenyl isocyanate (MDI).

However, despite the use of such pipeline coating compositions and materials, external corrosion of pipelines are a concern, when there is a breach of the coating, called a "holiday."

To protect against external corrosion, pipelines (and other buried structures) are typically cathodically protected in addition to being coated as described above. The cathodic protection (hereafter alternatively referred to as "CP") system is designed to protect the pipe where coating defects occur. Cathodic protection, as it is used here, refers to the phenomenon and practice of applying a small potential to a metallic pipeline that is buried in the ground. This imparted cathodic potential of the buried pipeline will tend to limit or protect against corrosion attacking the metal surface.

Cathodic protection provides corrosion protection to any bare metal areas exposed to soil due to coating defects or "holidays" by causing direct current to flow from the soil into the structure, thereby polarizing the structure as a cathode. Protection is ensured by modifying the environment around the steel as well as reducing the dissolution rate of the steel by reducing the anodic overpotential. The required direct current output of the cathodic protection system is reduced to manageable levels by the coating, which substantially reduces the bare metal area of the structure exposed to soil.

Two cathodic protection systems are generally in use for corrosion protection of metal structures. The first, termed an impressed current cathodic protection system, consists of a rectifier, insulated wires connecting the plus terminal of the rectifier to a buried anode (for instance graphite cylinders), insulated wire connecting the negative terminal of the rectifier to the protected structure, and test stations installed at the structure. The test stations typically consist of a pipe or a valve box with one or two insulated wires attached to the structure, typically by brazing, and a terminal board for termination of the wires. The test stations are used for monitoring the corrosion protection levels by measuring potentials between the structure and a reference electrode in an electrical contact with ground above the structure. The reference electrode usually consists of a copper rod fixed in a plastic body filled with saturated copper-sulfate solution, and having a porous plug to facilitate electrical contact with the ground.

The second, termed a sacrificial (galvanic) cathodic protection system, consists of magnesium, zinc or aluminum anodes buried next to the structure and often directly connected by an insulated wire to the structure. The protective current is generated by the potential difference between the structure and the anode. The structure with sacrificial anodes also has test stations for the cathodic protection testing and evaluation of its corrosion protection effectiveness.

Details of different cathodic protection systems and of the pipeline potential measurements can be found in W. von Baeckmann et al., *Handbook of Cathodic Corrosion Protection, Theory and Practice of Electrochemical Protection Processes* $3^{rd}$ Ed., Houston, Tex.: Gulf Publishing Co., 1997, the entire disclosure of which is incorporated herein by reference.

Even when cathodic protection is used, corrosion and defects tend to still occur. Coating defects generally take the form of either exposed bare steel or a disbondment where the coating remains intact but a gap is formed between it and the bare steel. CP systems effectively deliver current to defects directly exposed to soil or water and therefore mitigate corrosion. However, defects covered by a disbonded coating are sometimes difficult to protect because the coating shields the CP current from reaching deep inside the crevice (i.e., disbanded region). In addition, stress corrosion cracking and localized corrosion have been observed predominantly under disbanded regions of the pipe.

To determine the level of CP required for protection (in accordance with NACE standard RP0169), voltage measurements are taken of a pipe versus a reference electrode placed on the soil surface. CP coupons are samples of steel that are electrically bonded to the pipeline and CP system and simulate bare steel coating defects exposed to the soil. Briefly disconnecting the coupon from the pipe while measuring the potential of the coupon with respect to the soil, eliminates the ohmic resistance induced potential drop errors associated with coupon potential measurement. The limitation to this design is that only one geometry is represented by the simulated defect, while pipelines have a broad spectrum of defects. The most poorly represented pipeline coating defects are those under disbonded coatings.

Various CP systems are known in the art, as are coupons for assessing and measuring the CP systems. For example, CP system coupons are disclosed in U.S. Pat. Nos. 5,814,982, 6,060,877, and 6,107,811, the entire disclosures of which are incorporated herein by reference.

U.S. Pat. No. 5,814,982 discloses a test station for measuring the effectiveness of cathodic protection. The test station includes a cylindrical plastic reference tube extending downward through the soil to near the protected structure, such as a pipe. Two plastic coupon tubes extend within the chamber of the reference tube and are attached to opposite sides of interior sidewalls of the chamber. First and second circular cylindrical rod-shaped coupons are attached to, and sealed against, the bottom ends of the coupon tubes. A first coupon is electrically connected to the pipe, and the second coupon is used to measure a free-corrosion (native) potential.

U.S. Pat. No. 6,060,877 discloses a flat cathodic protection test probe. The probe comprises a non-metallic probe body with a mounted metal coupon simulating a large coating holiday on a pipeline, an insulated wire attached to the coupon for an electrical connection to the pipeline, a non-metallic tube filled with a conductive backfill, and a narrow and long porous potential sensing strips mounted flush with the coupon exposed surface in the central area of the coupon. The coupon is electrically insulated from the conductive backfill by a non-metallic coating and an epoxy compound for electrical insulation. To determine if the pipeline is fully cathodically protected, the flat cathodic protection probe is buried next to the pipeline and interconnected by the insulated wires with the pipeline. The potentials taken on the probe will not include a substantial voltage drop in soil and will not be adversely affected by shielding of the coupon by a reference electrode or its access tube to invalidate the reading. To measure the probe potential, a calibrated reference electrode is lowered into the tube to make an electrical contact with the conductive backfill and a high impedance voltmeter is connected to the coupon and to the reference electrode. No interruption of the cathodic protection to the pipeline or coupon is necessary.

U.S. Pat. No. 6,107,811 discloses an automated coupon monitor for detecting the electrical parameters associated with a pipe, a coupon and a reference electrode utilized with a cathodic protection system. A voltage detector circuit has its output applied to a pair of sample and hold circuits, one for recording $E_{OFF}$ and the other for recording $E_{ON}$. Connected in series between the coupon and the pipe is a zero resistance current detector circuit and an interrupter switch for measuring the pipe-coupon current and periodically interrupting that current to permit measurement, sampling and storing of $E_{OFF}$. The sample and hold circuits and the interrupter switch are controlled by a microprocessor controller. The circuit provides DC level outputs which can be easily read by a digital multimeter or stored in a data logger for subsequent reading or transmission to another location.

U.S. Pat. No. 5,728,943 describes the use of a plurality of mechanically stressed coupons maintained at various potentials to monitor stress corrosion cracking of pipeline. However, such a method does not recognize the fact that most stress corrosion cracking occurs under a disbanded coating and therefore does not provide a method to monitor conditions under a disbonded coating.

SUMMARY OF THE INVENTION

However, despite the above-described methods and materials for protecting a pipeline from corrosion, and for monitoring any corrosion that may occur, improvements in the pipeline industry are still desired. For example, the above-described references, while describing various coatings and CP systems, do not relate to measuring the effects of CP under disbanded coatings. Thus, the described coatings and CP systems do not provide any means to non-destructively determine the effectiveness of the coatings and systems, particularly with respect to disbonded coatings.

Unfortunately, the most susceptible location for corrosion and stress corrosion cracking on a pipeline with CP that meets standard protection criteria is underneath disbanded coatings. Successful development of a disbanded coating CP coupon would have wider application than conventional CP coupon because potential cannot be measured under disbondments for all coated pipelines (and not only for those where all sources of current cannot be disconnected).

Since most U.S. pipelines are coated and meet industry standard CP protection criteria (mandated in the United States by 49 C.F.R. Parts 192 and 195), a need exists for monitoring corrosion protection levels under disbanded coatings. No method presently exists to detect the onset of corrosion (including stress corrosion cracking) in the most vulnerable locations on pipelines, i.e., in the area of disbonded coatings.

In addition, accurate measurement of potential would allow a pipeline operator to determine if mitigation methods are effective. The simplest and least expensive mitigation is to apply more CP current by adjusting rectifier output or adding more sacrificial anodes. Sensing pH would provide an additional criterion to assess if corrosion is occurring underneath disbondments.

The only present methods to detect corrosion under disbanded coatings are inspection (e.g., smart pigs) and post failure analyses. Both of these methods find metal loss after the corrosion damage has already occurred; a disbonded coating coupon would be used to detect the onset of damage before significant metal loss occurs. A disbonded coating coupon might also provide historical information on changes under a disbondment. For example, in locations where stress corrosion cracking has been detected, the only information available is the post-failure analysis of the solution drawn from under the disbanded coating after excavating the pipe. Such an analysis may not accurately reflect the changes in the environment prior to cracking and may be affected by the excavation and extraction operations. For regulatory compliance, operators can use the tool to demonstrate the effectiveness of CP at a particular location given a range of coating disbondments.

DETAILED DESCRIPTION OF PREFERRED EMBODIMENTS

A coupon is designed and assembled to monitor cathodic protection (CP) under disbanded coatings. The coupon of the present invention is unique because it includes a simulated coating disbondment on a buried (or submersed) coupon and employs sensors not previously employed in this application. The coupon geometry is designed to represent a buried or submersed structure with CP where coating has disbonded. The design simulates a realistic coating disbondment and allows measurement of potential and pH inside the crevice free from IR drop errors.

According to the present invention, the coupon can take the form, size and shape of any of various coupon designs, including such form, size and shape of coupons that are conventionally used in the art. Suitable exemplary coupon designs are shown in FIGS. 1a–1b.

Figure 1A:
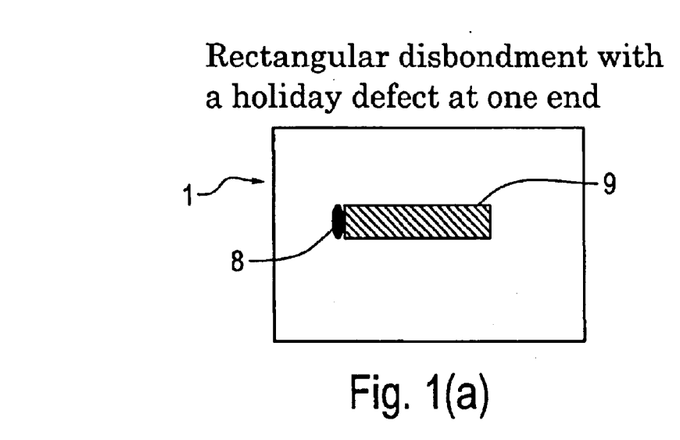
FIGS. 1a–1c show various exemplary coupon designs according to the present invention.
Figure 1B:
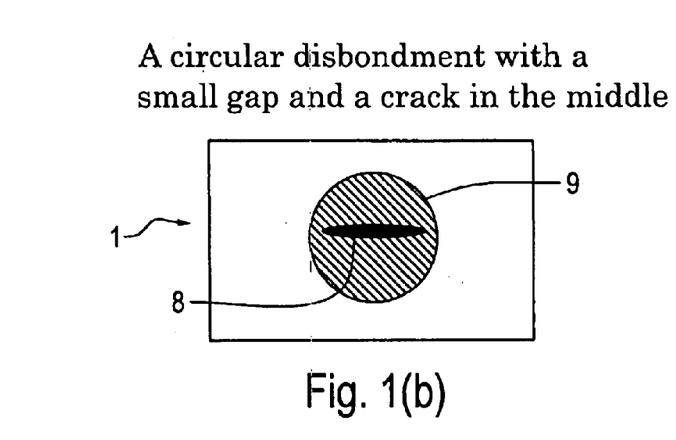
Figure 1C:
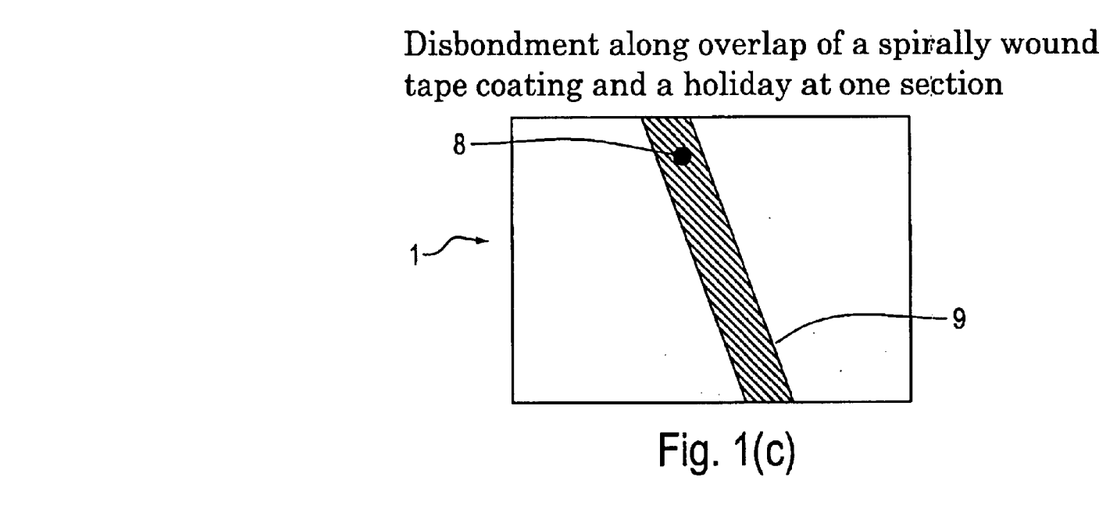

FIG. 1a depicts an exemplary coupon design in the form of a coupon 1 having a rectangular disbondment 9 with a holiday 8 at one end. FIG. 1b depicts an exemplary coupon design in the form of a coupon 1 having a circular disbondment 9 with a small gap and a crack forming a holiday 8 in the middle. FIG. 1c depicts an exemplary coupon design in the form of a coupon 1 having a disbondment 9 along an overlap of a spirally wound tape coating and a holiday 8 at one section. Other designs, of course, will be readily apparent to one of ordinary skill in the art based on the present disclosure.

The coupon can include one or more disbondment geometries, can include one or more sensors, and can include any other testing means that are suitable for coupon placement and use. Furthermore, if desired, multiple coupons, of identical or different design, can be used in the same environment or immediate pipeline area to monitor multiple or different geometries.

More than one type of disbondment geometry can be included on a coupon to simulate the variety of disbondments present on a pipeline. Thus, the disbondment geometry, and type, number and location of sensor placement, is in no way limited to the specific embodiments described herein.

A coupon is thus provided that simulates at least one, and optionally more than one, common disbanded coating defect geometry. Although in no way limited thereto, an exemplary embodiment of a coupon 1 is shown in schematic form in FIG. 2. A disbondment, in the form of a long narrow disbondment, is created with an opening adjacent to an exposed holiday. A polyethylene heat shrink sleeve 4 (with mastic (not shown) underneath) serves as the insulating coating expected to shield CP.

The coupon assembly 1 is manufactured using ordinary pipeline materials, although other materials can be used. Thus, for example, the coupon of FIG. 2 includes a length of ordinary pipe commonly used in pipelines and like structures. Preferably, the pipe is formed of the same pipe material as the pipeline that is to be monitored, to provide more accurate and useful measurements. As would be the case in many pipeline and similar environments, the pipe segment includes the bare metal pipe segment, typically with the bare metal 2 (shown in the disbondment/holiday potion) coated with a material such as a coal or epoxy coating 3. The pipe segment is likewise typically overcoated by a conventional corrosion protection material, such as a polyethylene heat shrink sleeve 4.

Figure 2:
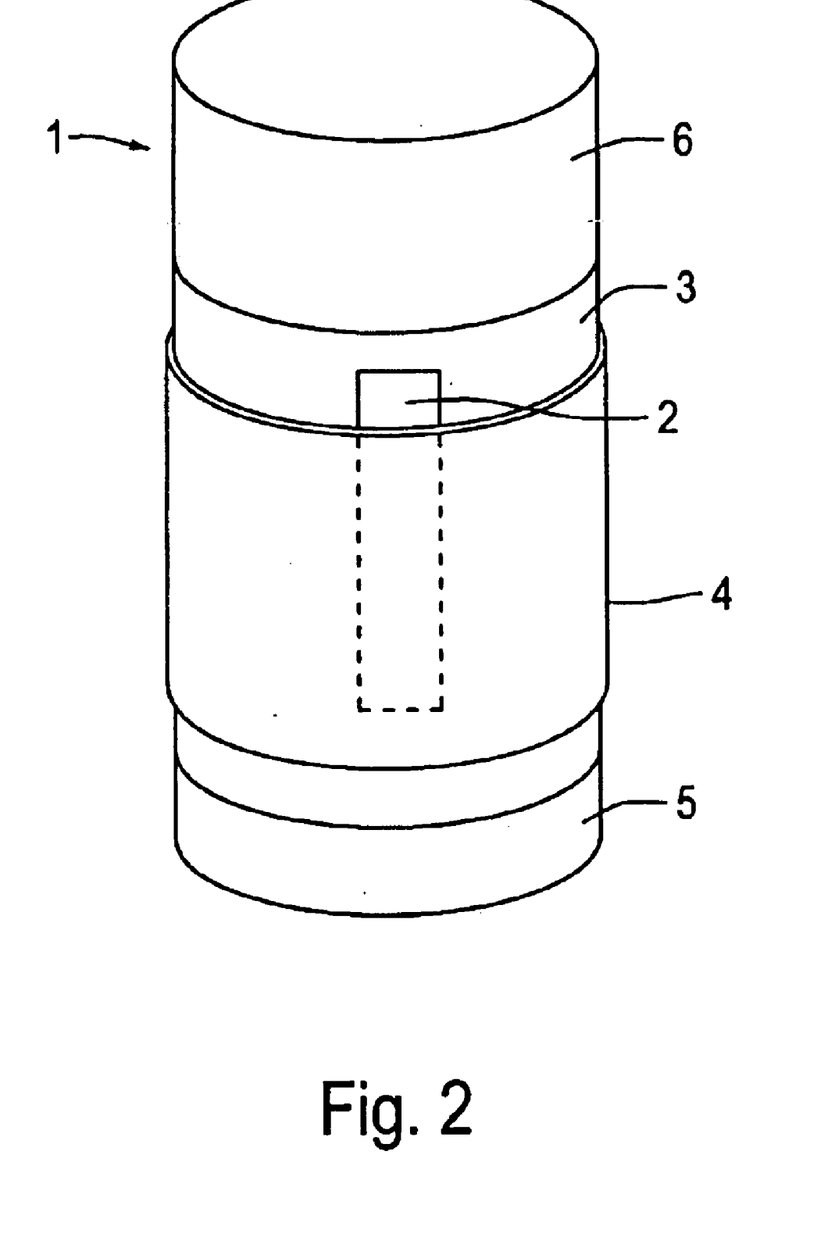
FIG. 2 shows a schematic of disbanded coating cathodic protection monitoring coupon.

Although the coupon could be used in such a form, the coupon of the present invention is particularly adapted to be connected to the pipeline itself. In such instances, it is common for one end of the coupon to be sealed, such as by a plug 5, and for the other end of the coupon to include a connection section 6. For example, the plug 5 and connection section 6 can be formed of a suitable material, such as either conventional pipe material, PVC, or the like. The connecting section 6 made of PVC or other insulating material provides a convenient enclosure from the coupon burial depth to the ground surface for electrical connectors so that the electrical measurement can be made above ground or remotely. The seal plug 5 prevents entry of ground water into the inside surface of the pipe which may negate the measurements by diluting the disbonded region or may harm the electrical connections. When the coupon is not to be directly connected to the pipeline, both ends of the coupon can be sealed, for example, by a suitable plug. The buried end of the coupon is either sealed completely or has a porous plug to allow electrolyte communication without flooding the coupon inner diameter. The porous plug can be used to insert a reference electrode, if desired.

Figure 3:
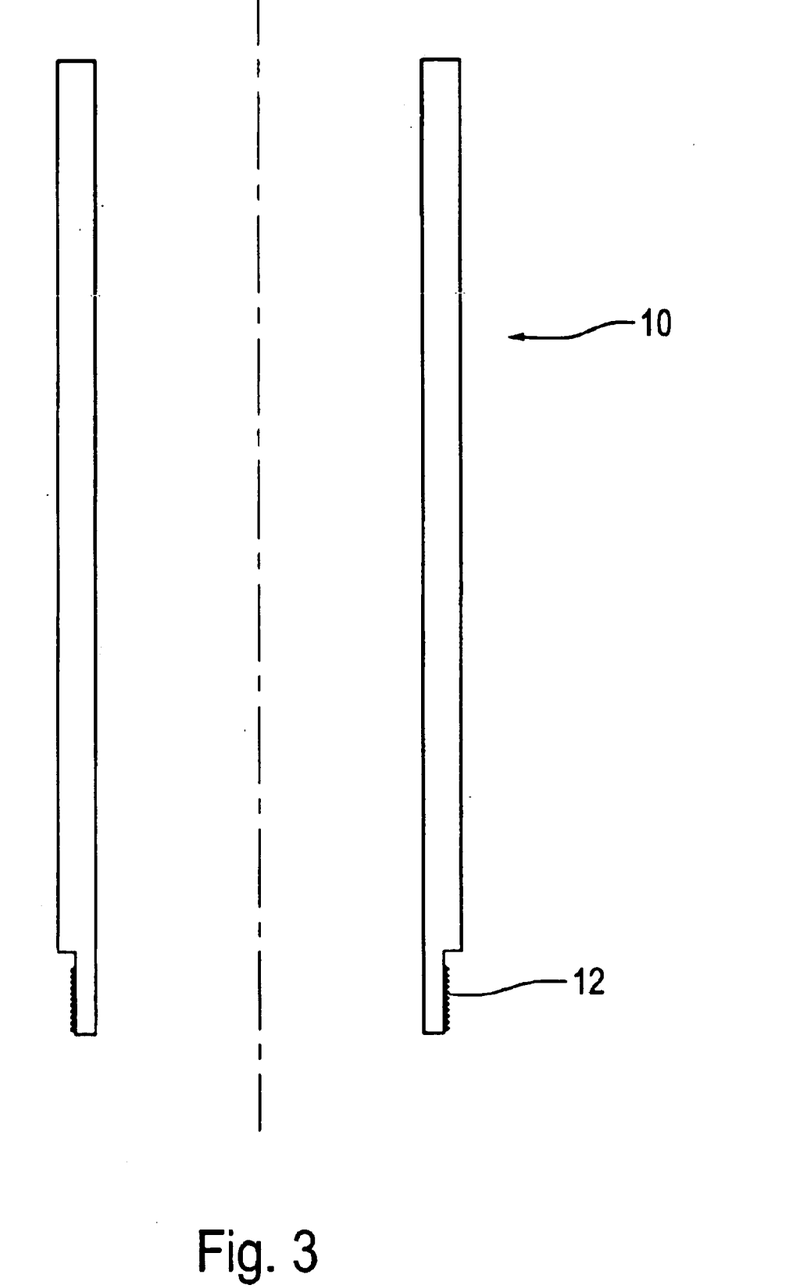
FIG. 3 shows internally threaded ends of the coupon.
Figure 4A:
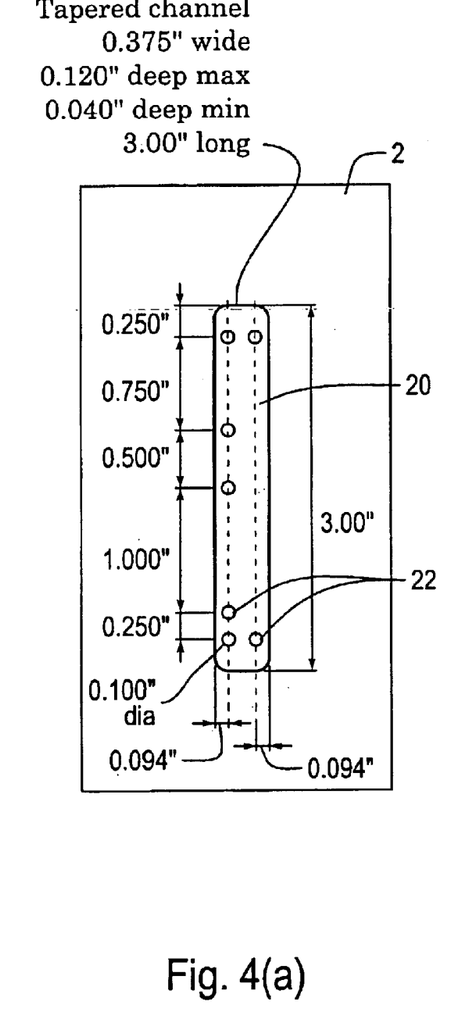
FIGS. 4a and 4b show a recessed defect formed in the coupon.
Figure 4B:
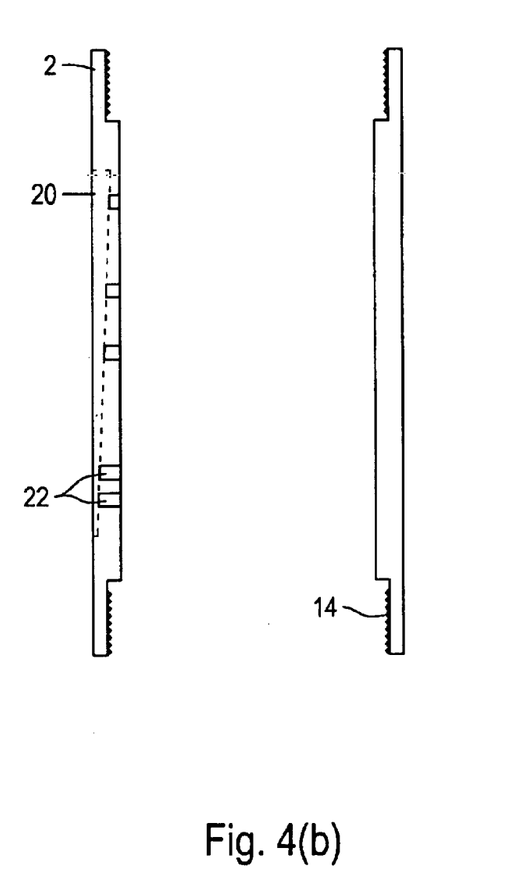

The plug and/or connection portion can be attached to the pipe segment of the coupon by any suitable means, including welding, chemical adhesion, physical coupling, and the like. For example, the plug and/or connection portion can be attached to the pipe segment of the coupon by providing suitable matching male and female screw threads (as shown in FIGS. 3 and 4b) on the respective portions, as is known in the art. FIG. 3 shows an example of a PVC pipe segment, suitable for attachment to the pipe segment in forming the coupon. The PVC pipe segment 10 includes threads 12 (with matching threads 14 on the pipe segment, as shown in FIG. 4b) to allow attachment to the pipe segment, although other attachment means can be used, as described above.

In assembling the coupon according to the present invention, any suitable pipeline material may be used as the pipe segment. In embodiments, the pipe segment can be selected from any of the available materials, ranging in nominal diameter of from ⅛ in. or less to 30 in. or more. The pipe segment can be made of any suitable pipe material, including but not limited to iron or ferrous materials, including cast iron, malleable iron and high silicon iron; carbon steel and low- and intermediate-alloy steels; high-alloy (stainless) steels; nickel and nickel-based alloys; aluminum and aluminum alloys; copper and copper alloys; titanium and titanium alloys; zirconium and zirconium alloys; tantalum; mixtures thereof; and the like. Thus, for example, any of the known or after-developed ferrous pipe materials can be used, such as by way of example only, Schedule 80, AP15L Grade B pipe.

Of course, although the above discussion focuses on the coupon including a pipe segment and being in the form of a pipe, the present invention is in no way limited to such an embodiment. Rather, the coupon of the present invention can take any suitable or desired shape and size. For example, the coupon can be in the form of a flat, curved, bent or the like plate. Where a plate is used, the disbondment coating geometries can likewise be formed in one or more faces of the plate, and suitable electrodes, sensors, or the like attached thereto.

Likewise, although the above discussion describes that a PVC plug and PVC segment are mated to the pipe segment, the materials are not limited to PVC, and any suitable material can instead be used. Suitable non-metals include, for example, thermoplastics, reinforced thermosetting resins, asbestos cement, borosilicate glass, impregnated graphite, and the like. For example, suitable thermoplastic materials commonly used in pipeline production include, but are not limited to, acrylonitrile-butadiene-styrene (ABS), cellulose-acetate-butyrate (CAB), chlorinated polyether, polyacetal, polyethylene, polypropylene, polyvinyl chloride (PVC), chlorinated polyvinyl chloride (CPVC), polyvinylidene chloride, polyvinylidene fluoride, nylon, polybutylene, polyphenylene oxide, mixtures thereof, and the like.

To form the coupon according to the present invention, one or more coating disbondments can be formed in the surface of the coupon. Thus, for example, the disbondment can be formed by machining a recess or holiday into the surface of the coupon. In the case of a pipe segment, the disbondment can be machined into the surface of the pipe segment to expose an area of the bare pipe material, prior to applying the corrosion protection coating. For example, FIGS. 3a and 3b show a disbondment area 20 machined into the surface of the pipe segment 2. FIGS. 3a and 3b show sensor holes 22 also formed in the disbondment area, and extending through the entire wall of the pipe segment 2. Cross-sections of the sensor holes are shown in FIGS. 4a and 4b. These holes are used to place sensors into the coupon to provide the desired disbondment area monitoring. Once the disbondment is formed, the pipe segment can be coated with a corrosion protection coating, if desired, as shown in FIG. 1. Where a corrosion protection coating is applied, it can be applied to either fully cover the formed disbondment area, or a portion of the disbondment area can be left exposed. In some embodiments, partially exposing the disbonded region simulates a holiday adjacent the disbondment. In other cases, such as in the case of a disbondment under a spiral wrap (see FIG. 1c), There may be no exposed disbondment region. Some coatings, such as fusion bonded epoxy coatings, may form only cracks, and no bubbling of the coating over the disbondment region (see FIG. 1b).

Although shown in FIGS. 4a and 4b as being a generally rectangular area with a sloping depth, the disbondment is in no way limited to such a configuration. FIGS. 4a and 4b show the disbondment in this manner as only one embodiment of the present invention. By machining the disbondment in this manner, a range of disbondment coating geometries can be monitored, where the respective disbondments effectively have varying underlying pipe thicknesses. However, it will be readily apparent that multiple disbondment geometries can be formed, each disbondment being provided with one or more sensors. Where multiple geometries are formed, it will likewise be understood that each geometry can be the same or different in terms of size, depth, exposure to the environment, and the like.

As described, the disbondment can be fitted with one or more sensors, to enable the desired measurement and/or monitoring of the conditions in the disbondment. Although not limited thereto, suitable sensors can include, for example, potential sensors (e.g., electrodes that monitor polarized potential or native potential), temperature sensors (e.g., thermocouples), solution chemistry sensors (e.g., sensors that monitor pH, solution conductivity, compositional analysis, and the like), and the like. In particular, a carbon steel electrode insulated from the rest of the coupon is used to monitor the native (i.e., no CP) potential. A tungsten/tungsten oxide electrode can be used as a rugged pH electrode. Other electrodes, such as iridinium/iridinium oxide electrode can also be used. A silver/silver chloride electrode can be used to monitor potential or chloride. Alternatively, a wicking material enclosed in a plastic tube may be used to communicate with a remote sensor at the ground surface. One or more such sensors can be used in the disbondment, as desired.

Figure 5A:
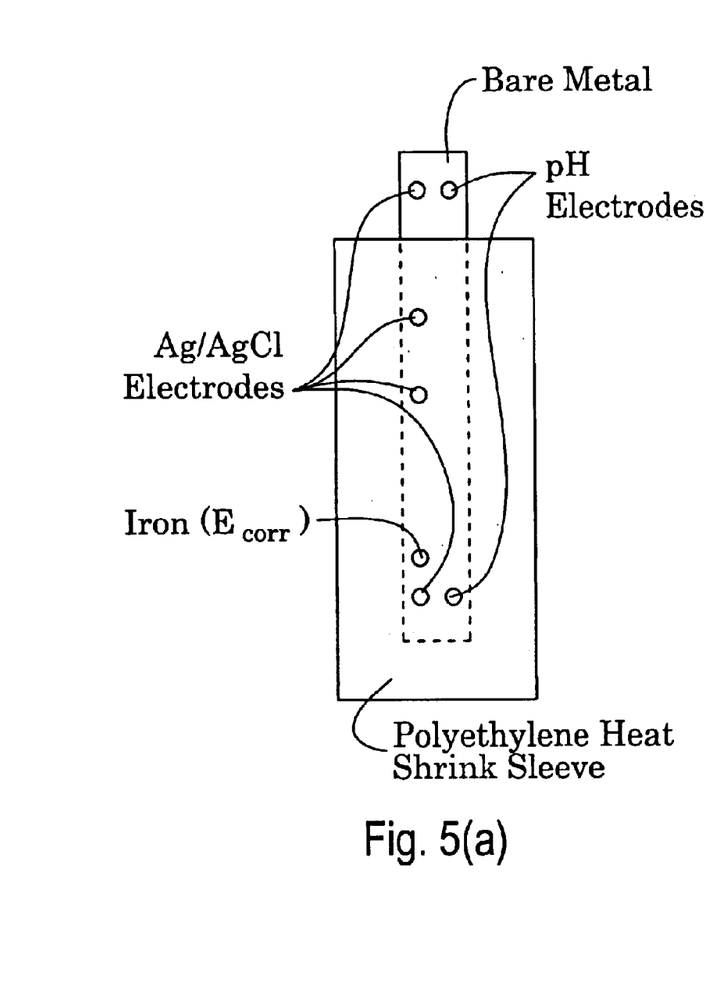
FIGS. 5a and 5b shows a final coupon design according to the invention.
Figure 5B:
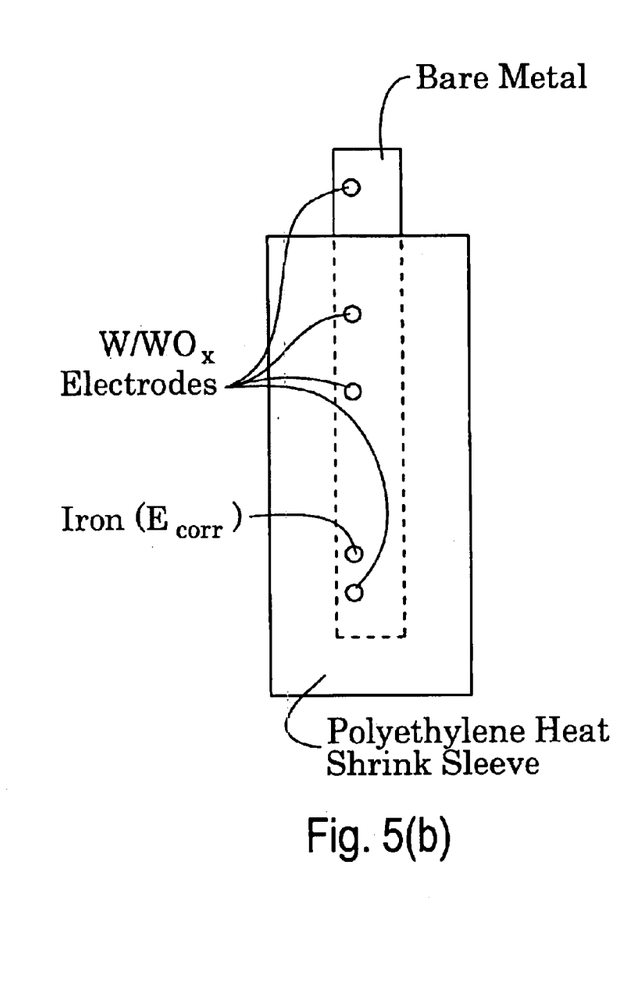

For example, and by way of example only, suitable electrode placement constructions are shown in FIGS. 5a and 5b. FIG. 5a shows a first prototype, which includes reference and pH electrodes known to be accurate in a laboratory environment. FIG. 5b shows a second prototype, which includes electrodes more suitable for field use. Of course, it is understood that the final coupon design will depend upon the particular environment, the properties sought to be measured, and the like.

In use, any free space within the coupon can be filled with a suitable backfill to provide a desired "salt bridge" in the coupon. Such conductive backfills are well known in the art, and can be readily prepared and used according to the present description. Although not limited thereto, a suitable backfill can be prepared from water and conductive soil or from water and a mixture of bentonite and sand.

According to the present invention, the coupon can be used in monitoring CP in any of the wide range of methods and systems that are well known in the art.

The present invention also provides methods for monitoring cathodic protection of various structures, such as pipelines. According to the methods of the present invention, a coupon such as described above is located near a pipeline or other structure to be monitored. Thus, for example, where cathodic protection of an underground buried pipeline is to be monitored, the coupon is likewise buried underground near the pipeline, and is appropriately connected to the pipeline, a cathodic protection source, and/or a monitoring station. Details of such monitoring methods are well known in the art, and thus are not further described herein aside from details regarding the coupon itself.

A particular advantage of the coupon of the present invention, however, is that active and accurate monitoring of cathodic protection can be conducted, even as to coating disbondment geometries. This in turn allows for non-destructive determination of the effectiveness of the corrosion protective coatings and systems, particularly with respect to disbanded coatings.

Although the coupon is described above with reference to specific materials and dimensions, it will be appreciated by one of ordinary skill in the art that the coupon can be made using any of a wide variety of materials, and in any of a wide range of dimensions. The present invention is not limited to the specific embodiments disclosed herein, and other embodiments are contemplated and within the scope of the invention.

EXAMPLES

In one specific non-limiting embodiment, as shown in FIG. 4a, the coupon itself is a 5-inch length of 2-inch nominal, Schedule 80, AP15L Grade B pipe. The ends are internally threaded as shown in FIG. 4b2 and mated to 2-inch nominal, schedule 80, PVC pipe on the top and a PVC plug on the bottom. A recessed defect is machined according to the drawings shown in FIGS. 4a and 4b. The defect is 3-inches long, 0.375-inches wide, 0.12-inches deep at the exposed holiday, and tapered to 0.04-inches at the end of the defect furthest down the length of the crevice. Small holes are drilled through the face of the defect to route sensors from the inside of the pipe to the disbondment environment. The pipe surface is blasted and coated with coal tar epoxy (brush applied), but any ordinary pipeline coating material and/or method could be used. A polyethylene heat shrink sleeve is then applied so that about 0.375-inches of the defect remain visibly exposed but the remaining length of defect is underneath the sleeve. The sleeve is applied with a propane torch, and care is taken so that the mastic does not flow into the disbondment area. Of course, other materials and methods can also be used to apply the heat shrink or comparable material.

Two prototypes are constructed with different sensor arrays. The first prototype uses reference and pH electrodes known to be accurate in a laboratory environment. The second prototype uses electrodes more suitable for field use. The final coupon design will utilize electrode sensors that measure polarized potential, native potential, and possibly solution chemistry (e.g., pH) as shown in FIGS. 5a and 5b.

Example 1

To determine if the defect geometry is suitable for simulating the effect of CP shielding, accurate, laboratory grade, electrodes are used to measure potential and pH. Ag/AgCl electrodes are made by anodically polarizing Ag wire in an HCl solution. See, for example, Brown, A. S., and D. A. MacInnes. 1935. *J. Am. Chem. Soc.*, 57. 2581. Conventional glass pH microelectrodes are used to accurately measure pH inside the crevice environment. An iron wire is used to measure free corrosion potential inside the crevice. This structure is shown in FIG. 5a.

Example 2

To make the coupon more field-applicable, the laboratory grade electrodes are removed. Tungsten/Tungsten Oxide, (W/WO$_x$) electrodes, which respond to pH, are inserted in place of the Ag/AgCl electrodes. See, for example, Dimitrakopoulos, L, et al. 1998. *Anal. Commun.*, 35. 395–398. The glass pH electrodes are removed. The potential distribution inside the crevice is measured by first measuring the potential of the W/WO$_x$ electrodes versus the coupon, and then measuring the potentials of the W/WO$_x$ electrodes in the current off condition (to eliminate IR-drop errors) using a remote electrode. The advantage to this approach is that potential can be accurately measured as a function of distance down the crevice regardless of how the embedded electrodes respond. The disadvantage is that a continuous electrolyte is required between the crevice and the remote electrode.

Testing Details:

The prototype coupon assembly is immersed in a tank filled with 50L of simulated ground water. Cathodic potentials are applied using a potentiostat (EG&G/PAR Model 273), a graphite counter electrode, and a saturated calomel electrode. Both potential and current density measurements are taken to demonstrate that the coupon could simulate shielding effects. The simulated ground water is about 10 kΩ-cm resistivity with dissolved solids concentration as shown in Table 1. High resistivity is chosen because conductive waters are less likely to support a potential gradient, and fresh water better represents onshore pipelines.

TABLE 1

Water Chemistry Used for Tests (about 10 kΩ-cm)

| Ion | mg/l |
| --- | --- |
| Bicarbonate | 18.0 |
| Sulfate | 5.0 |
| Chloride | 15.0 |
| Sodium | 9.5 |
| Calcium | 5.0 |
| Magnesium | 2.0 |
| Total Dissolved Solids | 54.5 |

Measurements that could be taken without current interruption are collected continuously over 1-month periods. Measurements requiring interruption are taken on an intermittent basis.

Figure 6:
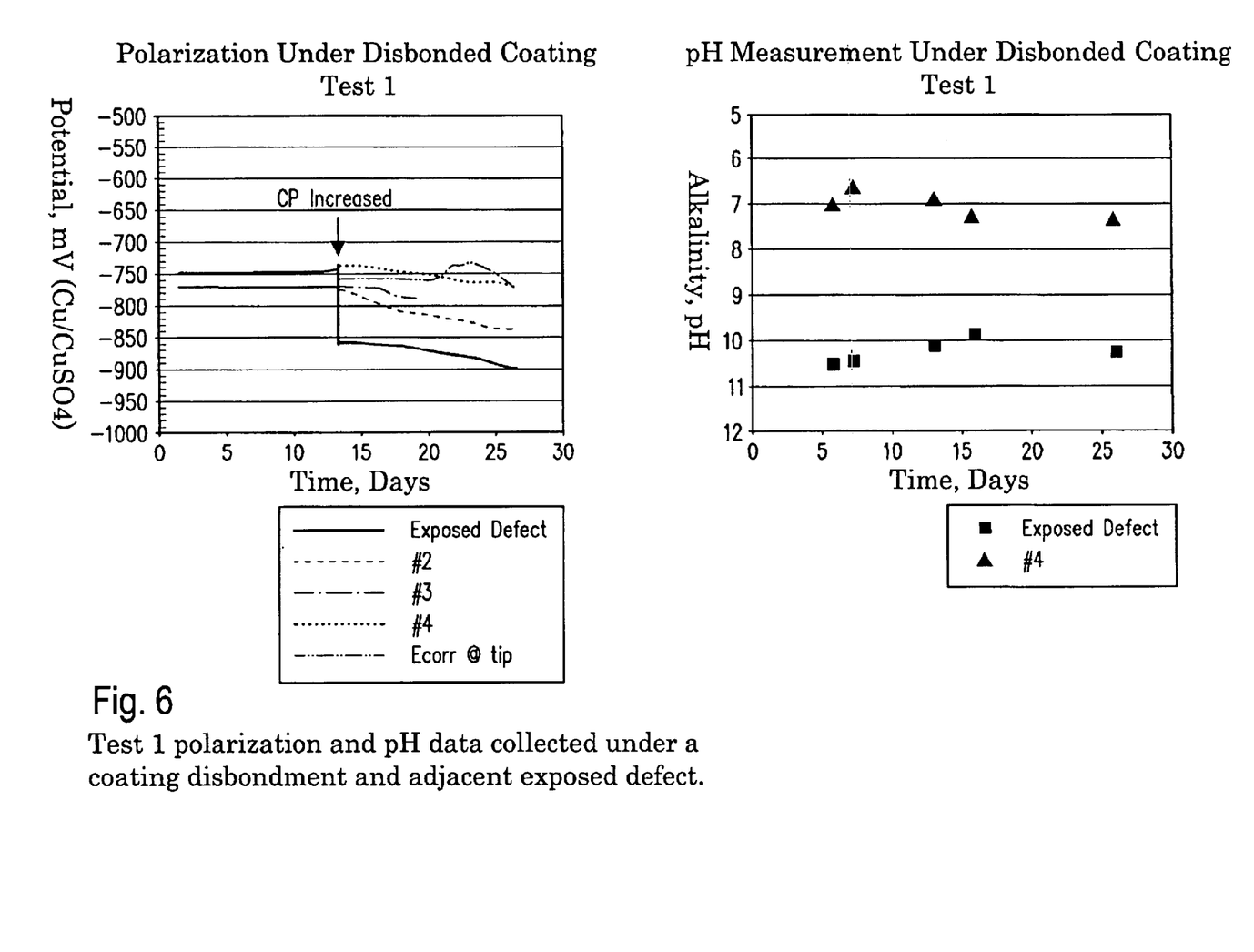
FIG. 6 shows test results of a coupon according to a first embodiment of the invention.
Figure 7:
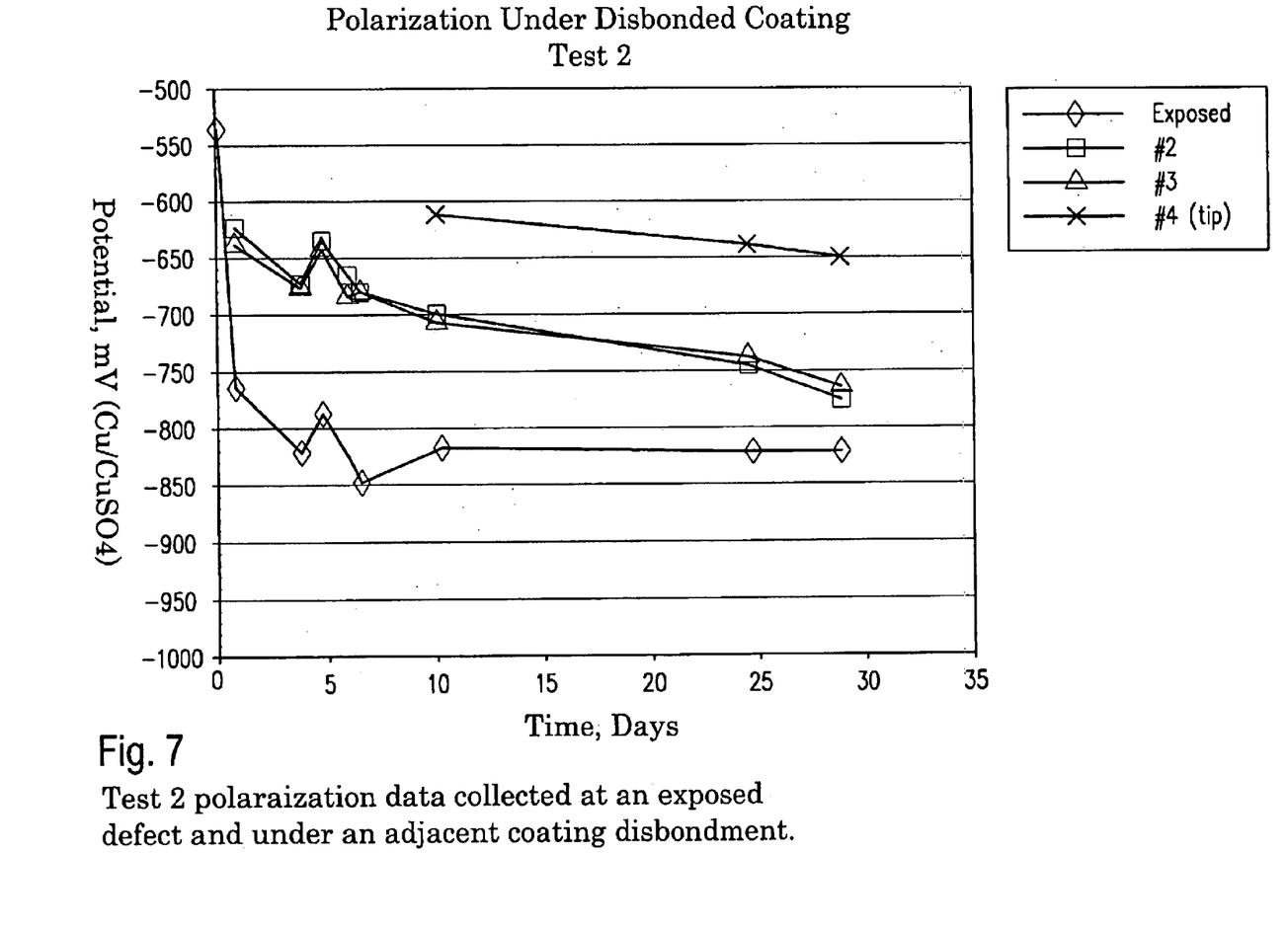
FIG. 7 shows test results of a coupon according to a second embodiment of the invention.

The results from Example 1 are shown in FIG. 6. The results from Example 2 are shown in FIG. 7. These figures illustrate the type of information that can be gained from these coupons, which is not possible from the measurements that are currently performed on pipelines.

While the invention has been described with reference to preferred embodiments, the invention is not limited to the specific examples given, and other embodiments and modifications can be made by those skilled in the art without departing from the spirit and scope of the invention.

What is claimed is:

1. A coupon for monitoring cathodic protection, comprising:

a metallic coupon structure comprising a substrate and a corrosion protective coating over at least a portion of the substrate, and at least one type of coating disbondment geometry anticipated on a pipeline fabricated on the outer surface of the metallic coupon structure between the substrate and the corrosion protective coating.

2. The coupon according to claim 1, wherein said metallic coupon structure comprises a steel structure coated at least partially with a corrosion protection coating.

3. The coupon according to claim 1, wherein the coupon is in a form of a pipe segment.

4. The coupon according to claim 3, wherein the disbondments are formed on an outer diameter of the pipe segment.

5. The coupon according to claim 1, wherein the coupon is in a form of a plate.

6. The coupon according to claim 1, wherein the coupon is formed from a material selected from the group consisting of pipeline and common grades of carbon steel.

7. The coupon according to claim 1, wherein the coupon is formed from a material selected from the group consisting of ferrous materials, carbon steel, low-alloy steels, intermediate-alloy steels, stainless steels, nickel, nickel-based alloys, aluminum, aluminum alloys, copper, copper alloys, titanium, titanium alloys, zirconium, zirconium alloys, tantalum, and mixtures thereof.

8. The coupon according to claim 1, wherein the coupon further comprises a section of plastic piping attached to said metallic structure.

9. The coupon according to claim 1, wherein the at least one coating disbondment is fabricated using a coating selected from the group consisting of pipeline coatings, a shrink sleeve used to repair pipelines or coat welded areas of pipelines.

10. The coupon according to claim 1, wherein the at least one coating disbondment is fabricated using a fusion welded coating.

11. The coupon according to claim 1, wherein the at least one coating disbondment is fabricated under overlapping sections of a spirally wound tape coating.

12. The coupon according to claim 1, further comprising at least one instrument selected from the group consisting of sensors and electrodes, said instrument positioned to monitor at least one property of said at least one coating disbondment.

13. The coupon according to claim 12, wherein the instrument is selected from the group consisting of potential sensors, temperature sensors, native potential sensors, and solution chemistry sensors.

14. The coupon according to claim 12, comprising a plurality of different instruments.

15. The coupon according to claim 12, wherein the instrument measures at least one of potential and pH in the at least one coating disbondment.

16. The coupon according to claim 1, wherein said coating disbondment geometry simulates a plurality of coating disbondments.

17. A method for monitoring cathodic protection, comprising locating a coupon according to claim 1 near a pipeline.

18. The method according to claim 17, wherein the coupon and the pipeline are buried underground.

19. The method according to claim 17, wherein the coupon and the pipeline are submersed in liquid.

20. The coupon according to claim 1, wherein the at least one type of coating disbondment geometry is fabricated by varying at least one selected from the group consisting of a length of the coating covering the metallic substrate, a gap between the coating and the metallic substrate, an area of exposed metal, and a shape of a coated area covering the metallic substrate.

* * * * *